United States Patent [19]

Lagow et al.

[11] Patent Number: 4,523,039

[45] Date of Patent: Jun. 11, 1985

[54] METHOD FOR FORMING PERFLUOROCARBON ETHERS

[75] Inventors: Richard J. Lagow, Austin, Tex.; Glenn E. Gerhardt, Wilmington, Del.

[73] Assignee: The University of Texas, Austin, Tex.

[21] Appl. No.: 563,013

[22] Filed: Dec. 19, 1983

Related U.S. Application Data

[63] Continuation of Ser. No. 139,181, Apr. 11, 1980, abandoned, which is a continuation-in-part of Ser. No. 901,905, May 1, 1978, abandoned.

[51] Int. Cl.$^3$ ............................................. C07C 41/01
[52] U.S. Cl. ................................... 568/615; 568/677; 568/683
[58] Field of Search .................. 568/615, 677, 683; 525/403, 471, 938

[56] References Cited

U.S. PATENT DOCUMENTS

| | | |
|---|---|---|
| 3,758,450 | 9/1973 | Margrave et al. . |
| 3,897,502 | 7/1975 | Russell et al. . |
| 3,985,810 | 10/1976 | von Halasz et al. . |
| 4,113,772 | 9/1978 | Lagow et al. . |
| 4,281,119 | 7/1981 | Lagow et al. . |

Primary Examiner—Howard T. Mars
Attorney, Agent, or Firm—Arnold, White & Durkee

[57] ABSTRACT

A method is disclosed for producing fluorocarbon ethers wherein a high molecular weight polyether is reacted with elemental fluorine to produce a highly fluorinated polyether which is subjected to an elevated temperature sufficient to cause fragmentation of the polymer chain to produce fluorocarbon ethers.

6 Claims, No Drawings

METHOD FOR FORMING PERFLUOROCARBON ETHERS

GOVERNMENT SUPPORT

The invention described herein was made in the course of work partially supported by grants from the United States Air Force.

RELATED APPLICATIONS

This is a continuation of application Ser. No. 139,181 filed Apr. 11, 1980 which itself was a continuation-in-part of U.S. Ser. No. 901,905 filed May 1, 1978, both now abandoned.

BACKGROUND OF THE INVENTION

1. Field of the Invention

This invention is in the field of fluorine chemistry and more particularly in the field of direct fluorination.

2. Description of the Prior Art

Saturated perfluoroplyethers are of current interest for new material applications due to their unusual properties. Lack of chemical reactivity and thermal stability are their outstanding features. These have been described as equally stable as perfluoroalkanes and unaffected over extended periods of time. See Henne, A. L., Richter, S. B., *J. Amer. Chem. Soc.*, 74, 5420 (1952); Henne, A. S., Smook, M. S., *J. Amer. Chem. Soc.*, 72, 4378 (1950); Banks, R. E., "Fluorocarbons and Their Derivatives:, MacDonald and Company, Ltd., London (1970) pp. 162.

The only reported reaction of saturated perfluoropolyethers is chain cleavage at the ether linkage by aluminum chloride, at elevated temperatures and autogenous pressure, to produce acyl chloride and trichloromethyl end-groups. See Tiers, G. V. D., *J. Amer. Chem. Soc.*, 77, 4837, 6703, 6704 (1955). These remarkable stabilities along with their interesting surface properties, viscosities and the broad liquid ranges of the low molecular weight compounds make saturated perfluoropolyethers attractive for numerous applications as solvents, hydraulic fluids, heat-transfer agents, lubricants, greases, sealants, elastomers and plastics. See Paciorek, K. J. L., Kaufman, J., Nakahara, J. H., Ito, T. I., Kratzer, R. H., Rosser, R. W., Parker, J. A., *J. Fluorine Chem.*, 10, 277 (1977); McGrew, F. C., *Chem. Eng. News*, 45, 18 (Aug. 7, 1967); Eleuterio, H. S., *J. Macromolecular Sci.—Chem.*, A6, 1027 (1972).

Synthetic methods have been limited in the preparation of saturated perfluoropolyethers. The most successful synthesis has been an anionic polymerization of perfluoroepoxides, particularly hexafluoropropylene oxide and tetrafluoroethylene oxide. See Hill, J. T., *J. Macromolecular Science—Chem.*, A8, 499 (1974); Eleuterio, H. S., *J. Macromolecular Science—Chem.*, A6, 1027 (1972). This synthetic procedure is a three-step scheme for saturated perfluoropolyether production involving oxidation of perfluoroolefins to perfluoroepoxides, anionic polymerization to acyl fluoride terminated perfluoropolyethers and conversion of acyl fluoride end-groups to unreactive end-groups by decarboxylation reactions or chain coupling photolytic decarboxylative reactions.

Other general synthetic methods of perfluoroether and perfluoropolyether production are the addition reactions of perfluorohypofluorite ($R_f$—O—F) with perfluoroolefins, and the perfluoroperoxide ($R_f$—O—O—$R_f$) addition reaction with perfluoroolefins and electrolytic fluorination in anhydrous HF of the corresponding hydrocarbon ethers. See, respectively, Porter, R. S., Cady, G. H., *J Amer. Chem. Soc.*, 79, 5625 (1967); Hohorst, F. A., Shreeve, J. M., *J. Amer. Chem. Soc.*, 89, 1809 (1967); Hohorst, F. A., Shreeve, J. M., *Inorg. Chem.*, 7, 624 (1968); Toy, M. S., Stringham, R. S., *J. Fluorine Chem.*, 5, 25, 481, (1975); Roberts, H. L., *J. Chem. Soc.*, 4538 (1964); Toy, M. S., Stringham, R. S., *J. Fluorine Chem.*, 7, 375 (1976); Burdon, J., Tatlow, J. C., *Adv. Fluorine Chem.*, 1, 129 (1960); Simons, J. H., U.S. Pat. No. 2,500,388 (1950), *Chem. Abs.*, 44, 5236b (1950); Simons, J. H. Brit. Pat. No. 659,251 (1951), *Chem. Abs.*, 46, 2934b (1952); Kauck, E. A., Simons, J. H., U.S. Pat. No. 2,644,823 (1953), *Chem. Abs.*, 48, 6469h (1954); Kauck, E. A., Simons, J. H., U.S. Pat. No. 2,594,272 (1952), *Chem Abs.*, 46, 6015a (1952).

Direct fluorination techniques have not been previously employed in the synthesis of perfluorocarbon ethers. This may be due to the fact that direct fluorination reactions involve elemental fluorine and are characterized by quick evolution of large quantities of heat, ignition and flaming which promote product decomposition, often with explosive violence. The inability to control direct fluorination reactions to produce high yields of the desired fluorinated reactant without concomitant fragmentation of the desired product has prevented direct fluorination from becoming a widely accepted method of fluorination. Because of these problems, a very diversified art has been developed to circumvent or obviate the use of fluorine gas by using inorganic metallic fluorides, hydrogen fluoride, or electrolytic cells where no free fluorine is provided.

A relatively recently developed process of direct fluorination, known as the LaMar process, has been used to fluorinate hydrogen-containing organic, organometallic and inorganic materials including polymers. In the LaMar process, the hydrogen-containing material is placed in a reaction chamber and an inert atmosphere such as helium is introduced. Fluorine gas or an inorganic fluoride is introduced into the inert atmosphere in a very low initial concentration such as not to exceed about 6% at the end of 30 minutes. The temperature is maintained at a uniform low temperature so as to avoid uncontrolled fluorination. The LaMar direct fluorination process is further disclosed in the following references, the teachings of which are hereby incorporated by reference. R. J. Lagow and J. L. Margrave, "Direct Fluorination of Organic and Inorganic Substances", *Proc. Natl. Acad. Sci.*, 67, 4, 8A (1970); R. J. Lagow and J. L. Margrave, "The Controlled Reaction of Hydrocarbon Polymers with Elemental Fluorine," *Polymers Letters*, 12, (April, 1974); A. J. Otsuka and R. J. Lagow, "The Direct Fluorination of Hydrocarbon Polymers", *J. Fluorine Chemistry*, (May, 1974); U.S. patent application Ser. Nos. 718,128 (1968), 133,804 (1971), 133,803 (1971), 133,865 (1971).

The LaMar process has also been extended to the fluorination of polyethers, such as polyethylene oxide, to produce perfluoroether oligomers having terminal carboxylic acid groups. In this technique, a polyether is placed in an enclosed reactor and maintained at a temperature below its decomposition point and subsequently directly fluorinated with a source of elemental fluorine until a perfluorinated polyether with terminal carboxylic acid groups is formed. This technique is described in U.S. Pat. No. 4,113,772, issued Sept. 12, 1978.

SUMMARY OF THE INVENTION

The invention described herein relates to a new synthesis for fluorocarbon ethers, including perfluorocarbon ethers. In this synthesis, a high molecular weight polyether, such as polyethylene oxide, is reacted with fluorine to produce a fluorinated polyether. During or subsequent to the fluorination reaction, the temperature of the reactor is raised to a temperature sufficient to cause fragmentation of the polymer backbone thereby producing lower molecular weight fluorocarbon ether compounds.

DESCRIPTION OF PREFERRED EMBODIMENTS

The starting material employed in the synthesis of this invention comprises a high molecular weight polyether. Poly(alkylene) ethers having a backbone of two or more carbon atoms can be employed. This includes polyethylene oxide, polypropylene oxide, and higher molecular weight analogues. Additionally, other polyethers, such as a copolymer of hexafluoroacetone and ethylene, can be used. Those skilled in the art will know other suitable polyethers, or be able to ascertain them using no more than routine experimentation.

The physical form of the starting polyether is not critical. It is preferred, however, to employ relatively fine powders to insure more complete fluorination, if the starting material is a solid.

Because of the tendency of fluorine to fragment materials, and because it is desirable to be able to produce highly fluorinated ethers, it is preferred to use LaMar fluorination techniques. In such techniques, small concentrations or quantities of fluorine are introduced initially to the material in the reactor to be fluorinated. One method for delivering these low concentrations is to dilute the fluorine with an inert gas, such as helium or neon. Alternatively, the fluorine can be introduced at very low flow rates until partial fluorination has been achieved, after which the flow rate can be increased.

The LaMar process allows for the control of the kinetics of the highly exothermic fluorination reaction and for the effective dissipation of the heat of reaction in order to minimize thermal degradation and skeletal fragmentation. The kinetics are typically controlled by using a mixture of fluorine gas highly diluted with helium (e.g., starting fluorine concentration generally 1-3% by volume) in a continuous gas flow system over a solid substrate. By limiting the amount of fluorine available for reaction, the reaction is slowed so heat evolution is controlled and effective heat dissipation is possible. Helium is used not only as a convenient diluent gas, but also, because of its relatively high heat capacity, as an effective heat dissipator. As the reaction proceeds, the partially fluorinated substrates become resistant to further fluorination by dilute fluorine mixtures, so more fluorine-concentrated gas mixtures are used to promote further reaction. The nature of the partially fluorinated substrates slows the reaction kinetics in the concentrated fluorine environments while efficient heat dissipation is still important for keeping skeletal fragmentation to a minimum. The result of a successful LaMar direct fluorination is conversion of a hydrocarbon substrate to a highly fluorinated compound, often perfluorinated, while completely maintaining the structural integrity of the carbon skeleton.

Fluorine gas is the preferred fluorinating agent and is available commercially at high purity levels. Other sources of fluorine, although not preferred, can be used, including chlorine trifluoride or bromine trifluoride. These latter sources of fluorine do, however, typically result in products which are partially chlorinated or brominated.

Solid reactants can be fluorinated at room temperature and atmospheric pressure in a horizontal cylindrical fluorine reactor. Such a reactor should be fabricated from materials which are inert to fluorine and the various other reactants. A suitable apparatus is described in U.S. Pat. No. 4,144,374, issued to Lagow et al, the teachings of which are hereby incorporated by reference. A heating element consisting of a resistance heater wrapped around the cylindrical reactor can be employed to elevate the temperature for fragmentation. Of course, those skilled in the art will recognize that other fluorination reactors could be employed.

Subsequent to or during production of the fluorinated polyether, this material is subjected to an elevated temperature. The elevated temperature is chosen to be sufficient to cause fragmentation of the polyether. Larger amounts of volatile perfluoroethers and nonvolatile oil may be produced by fluorinating and fragmenting the perfluoropolymer for longer times at higher temperatures. Higher temperatures also promote faster and more extensive fagmentation. It is this additional thermal activation energy supplied by the higher temperatures which makes fragmentation a significant process in the free-radical direct fluorination reaction. A suitable temperature range for most materials is between about 55° and 210° C., with a range of about 110° to about 200° C. being preferred for most materials, including fluorinated poly(alkylene oxides). Those skilled in the art will be able to ascertain, using no more than routine experimentation, operable and optimum temperatures for any given set of circumstances.

The mechanism of fragmentation is believed to involve chain cleavage at carbon-carbon bonds, but also must involve chain cleavage at carbon-oxygen bonds since the products have $CF_3$—$CF_2$—O end-groups. Chain cleavage occurring predominantly at the carbon-carbon bonds is consistent with the calculated bond strengths in perfluoroethers: C—C=80–90 K CAL, C—O=>100 K CAL.

The volatile products of the reaction can be transferred from a collection trap and separated by vacuum line trap-to-trap fractionation. Solid products can be Soxhlet extracted with a solvent such as diethyl ether. Glc assay of the volatile compounds can be used to isolate such compounds.

The LaMar direct fluorination and subsequent thermal cracking of polyethylene oxide can be illustrated as follows:

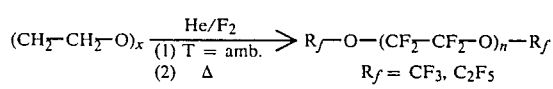

$$(CH_2-CH_2-O)_x \xrightarrow[(2)\ \Delta]{\underset{(1)\ T\ =\ amb.}{He/F_2}} R_f-O-(CF_2-CF_2-O)_n-R_f$$
$$R_f = CF_3,\ C_2F_5$$

The reaction of high molecular weight polyethylene oxide polymer with elemental fluorine, with reaction conditions chosen to promote fragmentation of the polymer during the fluorination process, has resulted in the synthesis of saturated perfluoropolyethers over a broad range of molecular weights. The low molecular weight compounds (n=1–6) which have been isolated are volatile liquids; medium molecular weight compounds are nonvolatile oils; and the high molecular weight compounds are gel-like and powdery solids. Milder fluorination conditions designed to prevent fragmentation led to an extremely stable high molecular weight perfluoropolyether. Of the specific perfluoropolyethers synthesized, only a few had been previously reported in the literature when methods other than direct fluorination were used.

The experimental results demonstrate that the direct fluorination of polyethylene oxide polymer is a useful synthetic method for production of perfluorethylene glycol ethers of low to very high molecular weights. An important feature of the method is that the reaction conditions employed govern the relative amounts of volatile liquid, nonvolatile oil and solid product that are formed. Fluorination of polyethylene oxide polymer at just ambient temperature resulted in conversion to perfluorinated polymer with only small amounts of volatile products formed by fragmentation. Fluorinations at ambient temperature then high temperatures resulted in perfluorination of the polymer at the ambient temperatures then fragmentation of the perfluoropolymer at the high temperatures to produce significant amounts of volatile perfluoroethers and extractable nonvolatile oil. Larger amounts of volatile perfluoroethers and nonvolatile oil may be simply produced by fluorinating and fragmenting the perfluoropolymer for longer times at the high temperatures. Higher temperatures should also promote faster more extensive fragmentation. It is the additional thermal activation energy available at the higher temperatures that makes fragmentation a significant process in the free-radical direct fluorination reaction.

The LeMar direct fluorination and subsequent thermal cracking of polypropylene oxide can be illustrated as follows:

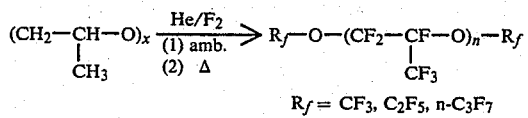

$$R_f = CF_3, C_2F_5, n\text{-}C_3F_7$$

Thus, the working hypothesis and synthetic strategy for polypropylene oxide was similar to those for polyethylene oxide. These included a "pre-fluorination" period, with reaction conditions chosen so that the structural integrity of the polymer was maintained while a significant number of hydrogens was replaced by fluorine, followed by a "fragmentation" period, in which higher temperatures promoted perfluorination and chain cleavage, to result in volatile perfluoropolyethers with perfluoro alkyl or possibly acyl fluoride end-groups.

The LaMar direct fluorination and subsequent thermal cracking of hexafluoroacetone-ethylene copolymer can be illustrated as follows:

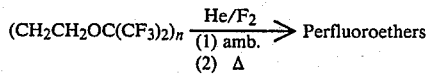

Here again, the strategy of a "pre-fluorination" period with conditions chosen to maintain the structural integrity of the polymer during fluorination followed by a "fragmentation" period at elevated temperatures to promote perfluorination and chain cleavage was employed.

Perfluoroethers with more than two backbone carbon atoms between successive oxygen atoms are interesting compounds that have been commercially unobtainable. Use of hydrocarbon polymers with the desired more than two carbon atom-one oxygen backbone repeating unit as fluorination substrates was limited by the lack of availability of such polymers. Tabata et al. have recently synthesized the above copolymer with a three carbon atom-one oxygen backbone repeating unit by the $^{60}Co$ radiation induced, low temperature copolymerization of ethylene and hexaacetone. See Tabata, Y., Ito, K., Oshima, K., Yamamoto, Y., "Advances in Chem. Series", No. 129, N. A. J. Platzer (ed.), (1973) Ch. 12. Their polymer is strictly a one to one alternating copolymer as indicated by the x-ray diffraction data for the crystalline polymer, the NMR data and the one to one consumption of monomers during polymerization that is independent of the ratio of monomers used.

The following examples more specifically illustrate this invention.

EXAMPLE 1

Solid polyethylene oxide polymer (Polysciences Inc., Grade 4,000,000) was ground and sieved to a fine powder (150 mesh). 6.53 g. was weighed into nickel boats and placed in a hollow nickel tube reactor formed from a 1½ inch OD nickel pipe 18 inches long with Teflon O-rings and flanges for closing the ends. The assembled apparatus was flushed with 100 cc/min of He overnight before the fluorine flow was started. The He flow rate was monitored with a Matheson Series 600 Rotameter flowmeter and the fluorine flow rate was controlled with a Monel needle valve and monitored wit a Hastings Mass Flow Transducer, Type F-50M. Fluorine was supplied by Allied Chemical Corporation and used without further purification. The reaction was carried out at the following gas flow rates and temperatures, (high temperatures were maintained with a heating tape and insulation):

| He (cc/min) | F$_2$ (cc/min) | Temp. (°C.) | Time (days) |
|---|---|---|---|
| 40 | 1.0 | amb. | 6 |
| 40 | 2.0 | amb. | 2 |
| 10 | 2.0 | amb. | 2 |
| 10 | 4.0 | amb. | 2 |
| 10 | 4.0 | 90 | 2 |
| 10 | 4.0 | 110 | 7. |

After the fluorine flow was terminated, the apparatus was again flushed with 100 cc/min of He overnight.

The gas mixture, after reaction, passed through a NaF pellet scrubber to remove the HF by-product, and then the volatile products were collected in a −196° C. trap. The volatile products of the reaction were transferred from the collection trap and separated by vacuum line trap to trap fractionation into four fractions: −78° (dry ice), −131° (pentane slush), −160° (iso-pentane slush) and −196°. The fractions were analyzed by infrared spectroscopy and Glc assay, and the separated pure compounds were identified by their infrared, NMR and mass spectra.

The solid product of the reaction was Soxhlet extracted with diethyl ether for two days. A low-volatility, low-viscosity oil separated as a heavier phase from the ether and was analyzed by NMR and infrared spectroscopy and elemental analysis, and its solubility in numerous hydrocarbon and fluorocarbon solvents was tested.

Glc assay of the volatile compounds was done on a ⅜" by 7 meter column packed with 10% Fluorosilicone OF-1-0065 on Chromosorb P. The gas chromatograph was a Bendix 2300 equipt with an automatic temperature programmer, and the carrier gas (He) flow rate was 150 cc/min. The infrared spectra were run on a Beckman IR-20A infrared spectrometer, the volatile compounds as gases in a 10 cm cell with KBr windows, the nonvolatile liquids as thin films between KBr windows and the solid product as a KBr pellet. The $^{19}$F NMR spectra were recorded on a Varian Associates A-56/60 NMR spectrometer set up for fluorine nuclei. The samples were run as neat liquids with Freon-11, $CFCl_3$, as an external reference. All samples were also checked for hydrogen atoms by $^1$H NMR spectroscopy with an A-56/60 set up for protons. The mass spectra of the volatile compounds were run on a Bell and Howel Model 21-491 mass spectrometer with the ion source cooled to room temperature and using the gas inlet system.

Low temperature melting points were measured by freezing the samples in a cold solvent in a transparent dewar, allowing the solvent to warm with stirring and monitoring the temperature with an Iron-Constantan thermocouple connected to a Leeds and Northrup Model 8690-2 Millivolt Potentiometer. Boiling points were measured with a micro boiling-point apparatus as follows: several drops of compounds were placed in a 4 mm tube attached to a thermometer at the bulb; a capillary tube was sealed 3 to 4 mm from the open end and placed open end down in the sample tube; the apparatus was immersed in an oil bath to above the sample level and heated until a steady stream of bubbles was established at the capillary tube; the setup was allowed to cool, and the temperature at which the bubbles stop and sample rises in the capillary tube is the boiling point of the compound. Elemental analyses were performed by Schwarzkopf Microanalytical Laboratories of New York City.

Volatile Products: Infrared analysis of the $-196°$ fraction of the volatile products indicated almost all of the sample was $CF_4$. Traces of $SF_6$ (presumably an impurity in the fluorine), $COF_2$, $C_2F_6$, and $SiF_4$ were also detected by infrared. The liquid volume of the fraction was estimated to be 1.2 ml., and assuming all of the material was $CF_4$, density 1.89 g/ml at 0183° C (The Merck Index), the isolated yield of $CF_4$ was 2.268 g. or 8.7 mole % of the starting polymer. This isolated yield is probably lower than the actual yield because $CF_4$ has a vapor pressure at $-196°$, and a significant amount could be pumped away during the vacuum line fractionation of the volatile products. $CF_4$ would also be lost by passing through the $-196°$ volatile product trap during the fluorination.

Infrared analysis of the $-160°$ fraction indicated $COF_2$ and $SF_6$ as the major components. The fraction was hydrolyzed to convert the $COF_2$ to $CO_2$, and the resulting gases were passed through a $-131°$ trap on a vacuum line to remove $CO_2$ and $H_2O$ from the water-stable gases of the fraction. The measured liquid volume of the fraction before hydrolysis was 1.8 ml and after hydrolysis was 0.2 ml. The 1.6 ml yield of $COF_2$, density 1.139 g/ml at $-114°$ C. (The Merck Index), is 1.83 g or 9.3 mole % of the starting polymer. The water-stable gases were separated further by Glc at $-50°$ isothermal. Only several mg of one compound, perfluoromonoglyme (which was combined with the perfluoromonoglyme from the $-131°$ fraction), was separated cleanly from the mixture. The rest of the mixture was analyzed by infrared which indicated predominately $SF_6$ with traces of $C_2F_6$ and perhaps $C_3F_8$ or $(CF_3)_2O$.

It was the Glc assay of the $-131°$ and $-78°$ fractions that resulted in isolation of significant amounts of fifteen volatile perfluoroethylene glycol ethers:

| | |
|---|---|
| $CF_3-O-(CF_2-CF_2-O)_a-CF_3$, | a = 1–6 |
| $CF_3-O-(CF_2-CF_2-O)_b-C_2F_5$, | b = 1–6 |
| $C_2F_5-O-(CF_2-CF_2-O)_c-C_2F_5$ | c = 1–3. |

The amounts and yields of the isolated pure perfluoroethers are listed in Table 1. (The compounds c = 1 and c = 3 were not isolated from the products of this particular reaction but were found in low yields in the products of preliminary reactions.) The material left unseparated by the Glc assay of the fractions was examined by infrared and showed C-H and -COF absorptions as well as the strong C-F absorption. This inseparable mixture contained the numerous branched, partially fluorinated and acyl fluoride terminated volatile fluoroethers that may be produced by the free radical fluorination reaction.

TABLE 1

Yields of Volatile Perfluoroethylene Glycol Ethers

| Compound | Milligrams (mg) | Wt. % of $-78°$ & $-131°$ fractions | Mole % of Starting Polymer* |
|---|---|---|---|
| a = 1 | 86 | 7.1 | .43 |
| b = 1 | 27 | 2.2 | .14 |
| c = 1 | — | — | — |
| a = 2 | 110 | 9.1 | .58 |
| b = 2 | 46 | 3.8 | .25 |
| c = 2 | 4.5 | 0.4 | .02 |
| a = 3 | 123 | 10.2 | .66 |
| b = 3 | 48 | 4.0 | .26 |
| c = 3 | — | — | — |
| a = 4 | 122 | 10.1 | .66 |
| b = 4 | 51 | 4.2 | .28 |
| a = 5 | 123 | 10.2 | .68 |
| b = 5 | 83 | 6.9 | .46 |
| a = 6 | 85 | 7.1 | .47 |
| b = 6 | 39 | 3.2 | .22 |
| Unseparated material | 256 | 21.3 | 1.38+ |
| Totals | 1.2045 g | 100% | 6.49% |

*Calculation: g compound/mw compound = moles compound, (moles compound) × (# Carbon atoms in structure) = moles carbon atoms, (moles carbon atoms in compound)/(moles carbon atoms in starting polymer) × 100% = mole % of starting polymer
+Calculated assuming an average MW of 500 and an average # carbon atoms per molecule of 8

The isolated compounds were characterized by $^{19}$F NMR and mass spectral analysis. The infrared spectra of the fifteen volatile perfluoroethers were all similar in showing strong, broad absorptions in the C-F stretching region, 1300-1100 cm$^{-1}$. (The infrared spectrum of perfluorotriglyme is included as representative of the C-F region.) The spectra also exhibited weaker absorptions in the "fingerprint" region, 1000-600 cm$^{-1}$, which are useful for compound identification. These weaker, fingerprint absorptions are listed for each compound in Table 2. No other infrared absorptions are observed except for the C-F overtone near 2400 cm$^{-1}$ when high gas concentrations are used.

TABLE 2

Infrared Absorptions in the Fingerprint Region of Volatile Perfluoroethylene Glycol Ethers

| Compound | Absorption Frequency (cm$^{-1}$)* |
|---|---|
| a = 1 | 925(w), 890(m), 865(w), 820(m), 690(m) |
| b = 1 | 910(w), 800(w), 730(m), 685(w) |
| c = 1 | 905(w), 845(w), 795(w), 740(w), 710(m), 695(sh) |
| a = 2 | 920(sh), 905(m), 765(m), 690(w), 675(w,sh) |
| b = 2 | 910(w), 765(w), 740(sh), 720(m), 690(w) |
| c = 2 | 765(w), 725(m), 705(w), 690(w) |
| a = 3 | 905(m), 790(w), 738(m), 685(w) |
| b = 3 | 910(m), 785(w), 745(m), 710(m), 695(sh), 685(sh) |
| c = 3 | 1000(w), 910(w), 785(w), 750(sh), 720(m), 710(sh), 695(m) |
| a = 4 | 910(m), 765(w), 725(w), 685(w) |
| b = 4 | 955(w), 910(w), 765(w), 735(m), 710(w), 695(w) |
| a = 5 | 910(w), 740(w), 720(sh), 705(sh), 685(w) |
| b = 5 | 905(w), 730(m), 690(w) |
| a = 6** | 1000(w), 905(m), 765(w), 730(sh), 685(m) |
| b = 6** | 995(w), 905(m), 765(w), 735(sh), 690(m) |

*Letters in parentheses indicate strength of absorption: w — weak, m — medium, sh — shoulder
**Not volatile enough to be run as a gas and have the fingerprint absorptions appear; run as a liquid film between KBr windows.

The $^{19}$F NMR data was the most useful information for structure determination. The following signal assignments were duduced from the spectra interpretation ($^{19}$F NMR reference-neat CFCl$_3$ external):

| | |
|---|---|
| CF$_3$—O | 59.4–58.9 ppm (triplet)   J = 9–10 Hz |
| CF$_3$—O—CF$_2$—CF$_2$ | 94.0–93.5 ppm (quartet) |
| CF$_3$—CF$_2$—O | 90.7–90.3 ppm (singlet) |
| Internal CF$_2$—O | 91.9–91.4 ppm (singlet) |
| CF$_3$—CF$_2$—O | Magnetically equivalent to internal CF$_2$—O |

For all compounds, the experimental relative intensities of the signals correspond exactly to the calculated relative intensities. No signals were observed for any of the compounds in $^1$H NMR scans. The $^{19}$F NMR data is listed in Table 3.

was m/e 300. When the spectra were run with the ion source cooled to room temperature, higher mass peaks up to the parent minus fluorine peak was observed for each compounds as follows:

| | |
|---|---|
| a = 1, 251 (C$_4$F$_9$O$_2$$^+$); | b = 1, 301 (C$_5$F$_{11}$O$_2$$^+$); |
| a = 2, 367 (C$_6$F$_{13}$O$_3$$^+$); | b = 2, 417 (C$_7$F$_{15}$O$_3$$^+$); |
| a = 3, 483 (C$_8$F$_{17}$O$_4$$^+$); | b = 3, 533 (C$_9$F$_{19}$O$_4$$^+$); |
| a = 4, 599 (C$_{10}$F$_{21}$O$_5$$^+$); | b – 4, 649 (C$_{11}$F$_{23}$O$_5$$^+$); |
| a = 5, 715 (C$_{12}$F$_{25}$O$_6$$^+$); | b – 5, 765 (C$_{13}$F$_{27}$O$_6$$^+$); |
| a = 6, 831 (C$_{14}$F$_{29}$O$_7$$^+$); | b – 6, 881 (C$_{15}$F$_{31}$O$_7$$^+$); |
| | c = 1, 351 (C$_6$F$_{13}$O$_2$$^+$); |
| | c = 2, 467 (C$_8$F$_{17}$O$_3$$^+$); |
| | c = 3, 583 (C$_{10}$F$_{21}$O$_4$$^+$); |

Chain fragmentation and rearrangement still persisted with the cooled ion source, and for the higher molecular weight compounds, the low m/e peaks had to be expanded off scale in order to observe the parent minus fluorine peaks. By far the most intense peaks of the mass spectra for all compounds were m/e 69, (CF$_3$$^+$) and 119, (C$_2$F$_5$$^+$) with higher mass peaks descending in intensity with increasing mass, a characteristic of many fluorocarbons. See Majer, J. R., Adv. Fluorine Chem., 2, 55 (1961). Other common lowmass fragments observed were: 31, (CF); 47, (CFO); 50, (CF$_2$); 97, (C$_2$F$_3$O); 100, (C$_2$F$_4$); 135, (C$_2$F$_5$O); 163, (C$_3$F$_5$O$_2$); 169, (C$_3$F$_7$); and 185, (C$_3$F$_7$O). The common higher mass fragments observed for the higher molecular weight compounds were of the general formulas C$_n$F$_{2n+1}$O$_x$ and C$_n$F$_{2n-1}$O$_x$.

The physical constants of the volatile perfluoroethers, including boiling points, melting points, and Glc retention times were determined. A graph of the boiling points versus compound mass produced a smooth curve. Boiling points were precisely measured with the mirco boiling point apparatus. No boiling points are reported for the compounds a, b, c = 1 because they are so volatile that the several drops of sample would evaporate from the micro boiling point apparatus before a boiling point could be determined. No melting points

TABLE 3

$^{19}$F NMR Signals of Volatile Perfluoroethylene Glycol Ethers
Shift in ppm vs. CFCl$_3$ ext.

| Compound | CF$_3$—O (t) | CF$_3$—O—CF$_2$ (q) | Internal —CF$_2$—O— (s) | CF$_3$—CF$_2$—O (s) | $^J$CF$_3$—O—CF$_2$ (Hz) |
|---|---|---|---|---|---|
| a = 1 | 59.4 | 94.0 | — | — | 10 |
| b = 1 | 59.4 | 93.9 | 91.9 (4) | 90.7 | 10 |
| c = 1 | — | — | 91.7 (4) | 90.5 | — |
| a = 2 | 59.3 | 93.8 | 91.8 (2) | — | 9 |
| b = 2 | 59.2 | 93.7 | 91.7 (8) | 90.5 | 9 |
| c = 2 | — | — | 91.6 (6) | 90.4 | — |
| a = 3 | 59.1 | 93.8 | 91.7 (4) | — | 9 |
| b = 3 | 59.0 | 93.7 | 91.6 (12) | 90.4 | 9 |
| c = 3* | | | | | |
| a = 4 | 59.1 | 93.7 | 91.6 (6) | — | 9 |
| b = 4 | 58.9 | 93.5 | 91.5 (16) | 90.3 | 10 |
| a = 5 | 58.9 | 93.5 | 91.5 (8) | — | 10 |
| b = 5 | 59.0 | 93.6 | 91.5 (20) | 90.3 | 10 |
| a = 6 | 59.0 | 93.6 | 91.4 (10) | — | 9 |
| b = 6 | 59.1 | 93.7 | 91.6 (24) | 90.4 | 9 |

*Insufficient compound isolated to obtain NMR spectrum.
t = triplet, q = quartet, s = singlet
Relative Intensities:
CF$_3$—O = 3
CF$_3$—O—CF$_2$ = 2
CF$_3$—CF$_2$—O = 3
Internal —CF$_2$—O— = as indicated in parentheses The mass spectra of the fifteen perfluoroethers were characterized by extensive chain degradation and rearrangement. In fact, with the ion source of the mass spectrometer at normal operating temperatures, the highest mass peak observed for any of the compounds are reported for the compounds, a, b, c = 1 and a, b = 2 because either a supercooling problem may have arisen, that prevented crystallization of the compounds even at temperatures much below the predicted melting points, or because the compounds froze as glasses which made visual distinction between the solid and liquid states impossible. The physical constants determined are given in Table 4.

TABLE 4
Physical Constants of Volatile Perfluoroethylene Glycol Ethers

| Compound | M.P. (°C.) | B.p. (°C.) | Glc Retention Time (min) Temp. Prog. A | Glc Retention Time (min) Temp. Prog. B |
|---|---|---|---|---|
| a = 1 | — | — | 2 | — |
| b = 1 | — | — | 4 | — |
| c = 1 | — | — | 6 | — |
| a = 2 | — | 66 to 66.5 | 11 | 4 |
| b = 2 | — | 81.5 to 82 | 22 | 6 |
| c = 2 | −78.5 to −77 | * | 34 | 8 |
| a = 3 | −82 to −80.5 | 104.5 to 105 | 44 | 11 |
| b = 3 | −80 to −78 | 117.5 to 118.5 | 58 | 18 |
| c = 3 | ** | * | 66 | 28 |
| a = 4 | −71 to −69.5 | 138 to 138.5 | 74 | 43 |
| b = 4 | −60.5 to −60 | 146.5 to 148 | 84 | 56 |
| a = 5 | −47 to −46 | 164 to 164.5 | 102 | 74 |
| b = 5 | −47 to −46 | 173.5 to 174 | 114 | 83 |
| a = 6 | −43.5 to −43 | 186 to 186.5 | 129 | 96 |
| b = 6 | −35 to −34 | 193 to 194 | 142 | 103 |

Temp. Prog. A: 0° for 20 min; 1°/min to 60°; 60° for 20 min; 1°/min to 120°
Temp. Prog. B: 30° for 30 min; 1°/min to 120°
*Insufficient compound isolated to obtain a B.P.
**Insufficient compound isolated to obtain a M.p.

Elemental analyses of a couple of compounds were done and considered representative of the results that would be obtained for the other compounds. The compounds chosen for elemental analysis were a=4, perfluorotetraglyme, and b=4 perfluorotetraethylene glycol methyl ethyl ether. The results were: for a=4, Calc. C-19.42%, F-67.64%, O-12.94%, Found: C-19.23%, F-68.48%; for b=4, Calc. C-19.76%, F-68.26%, O-11.98; Found: C-19.92%, F-69.32%.

Gas liquid chromatography (Glc) was used for separation of the volatile perfluoroethers because it has been proven to be the best method for separation of the fluorocarbons produced on an experimental scale. See Banks, R. E., "Fluorocarbons and Their Derivatives", MacDonald and Company, Ltd., London, pp. 16 (1970). Clearly, Glc is impractical for large scale separations, so fractional distillation was examined as an alternative separatory method. Several ml of volatile perfluoroether product mixture (from a previous reaction) was subject to fractional distillation, and the cuts of distillate were analyzed for composition by Glc. The boiling ranges of the fractions and the compounds that comprised each fraction are listed in Table 5.

TABLE 5

| Boiling Range of Distillate | Compounds and Relative Amounts in Distillate (by Glc) |
|---|---|
| 24–30 | a = 2 > b = 1 > c = 1 > a = 1 |
| 47–60 | a = 2 > b = 2 |
| 60–65 | a = 3 > b = 2 > a = 2 > b = 3 > c = 2 |
| 67–77 | a = 3~b = 3 >> b = 2~c = 2~c = 3~a = 4 |
| 88–93 | b = 3~a = 4 >> a = 3~c = 3~b = 4 |
| 100–108 | a = 4~b = 4 >> b = 3~c = 3~a = 5~b = 5 |

It can be seen from this data that the fractions are relatively poorly separated mixtures and distillation, as would be expected, is much less efficient than Glc for separation of pure compounds on an experimental scale. On a larger scale, where a larger, more efficient fractionation column could be used, distillation should be an adequate and preferred technique.

Solid Products: The solid product of the reaction, material remaining in the nickel boats in the reaction chamber, was first subject to Soxhlet extraction with diethyl ether for several days. A low-viscosity oil separated as a heavier phase from the ether. The 0.32 g of oil was removed, the ether (ca. 100 ml) was concentrated by distillation and an additional 0.27 g of oil was obtained. The extracted oil had a very low volatility: only a trace of material could be pumped into a vacuum line over a six hours at one micron pressure. The extracted oil was combined with 0.27 g of liquid that remained in the volatile product trap after pumping on the trap for several hours at one micron pressure. The combined material had a weight of 0.86 g. and a density of 1.79 g/cc.

The nonvolatile oil was analyzed by infrared of a thin liquid film and by $^{19}F$ NMR. The infrared spectrum showed bands at (absorptions in cm$^{-1}$) 1300–1000 (s, broad), 1000 (w), 955 (w), 910 (m), 810 (sh) and 685 (m), a spectrum almost identical to those of the higher molecular weight volatile perfluorethers. The $^{19}F$ NMR spectrum showed signals at 58.7 ppm (t) J=9 Hz, 93.3 ppm (q) J=9 Hz, 91.3 ppm (s), 90.0 ppm (s), (the signals exhibited by the volatile straight-chain perfluoroethylene glycol ethers), and much weaker, broad signals at 128.1 ppm and 125.8 ppm and 89.5 through 82.5 ppm. The $^{19}F$ NMR spectrum was unchanged after washing the sample with concentrated aqueous base, and no $^1H$ NMR signals were detected. The weak, broad signals observed are believed due to fluorine nuclei at chain-branching or cross-linking sites from crosslinked species which are present in extremely low yield in the mixture. Integration of the NMR signals indicates the weak signals represent a small, insignificant amoung of the sample. Ignoring these weak signals and using the integrated intensities of the major signals due to the straight-chain perfluoroethers, an average molecular weight of the mixture may be determined by NMR end-group analysis. Such analysis indicates 8.2$CF_2$ groups per $CF_3$ group, or MWav.=1080, average degree of polymerization is 8 and the average number of carbon atoms per molecule is 18. The yield of nonvolatile perfluoroether oil (calculated as in Table 1) was 4.9 mole % of the starting polymer.

The solid product, after ether extraction, was dried, and visual examination indicated it was a mixture of two types of material. Most of the solid was a fluffy, sticky, white, amorphous powder, but a significant number of small chunks of translucent, gel-like material exhibiting rudimentary elastomeric properties was also observed. Infrared analysis of the powder (KBr pellet) produced another spectrum almost identical to the spectra of the higher molecular weight volatile perfluoroethers and the nonvolatile oil. The bands observed were: 1300-1100 (s, broad), 1000 (sh), 950 (w), 910 (w), 895 (sh), 760 (sh), and 690 (m). Elemental analyses were performed on samples of both powder and gel. The results for the powder were C-20.82%, F-66.37%, O-12.52%, and the results for the gel were C-20.79%, F-66.46%, O-12.20% (fluorine values reported as ±0.6% and oxygen values as ±1.0%). These results show no difference in the two types of solid product, and both sets of results are within experimental error of the calculated analysis of the $(CF_2CF_2O)_n$ structure. Thermal analysis of the gel on a DuPone 990 Thermal Gravimetric Analyzer indicates the material shows no melting point and is stable up to 300° C. At 370° C. a minor mode of decomposition occurs, major thermal decomposition begins at 400° C., and by 550° C. all of the sample had decomposed except for a small residue. The amount of solid product from the reaction was 9.78 g which is, based on the $(CF_2CF_2O)_n$ structure, 56.8 mole % of the starting polymer.

Further analysis and separation of the solid product was limited by its lack of solubility. Of the numerous organic hydrocarbon and fluorocarbon solvents tested, only two, perfluoro-2-butyltetrahydrofuran and 1,1,2-trichlorotrifluoroethane, showed slight solvation ability. Solvents were tested with heating and stirring over two to three day periods. Solubility was tested by centrifuging the mixture and examining the solution by $^{19}F$ NMR, looking for the internal —$CF_2$—O— signal near 91 ppm upfield from $CFCl_3$ and the $CF_3$—O— signal near 59 ppm upfield. For the two successful solvents, the $CF_3$—O— signal was barely detectable, and the —$CF_2$—O— signal was clearly evident but very weak compared to the solvent signals. Product solubility in both solvents was approximately the same and was calculated, by NMR integrated intensities, to be ca. 2.5 wt. %. Such limited solubility prevented average molecular weight determination of the solid product by NMR end-group analysis and the use of high pressure liquid chromatography for preparative separation.

In summary, the complete mass balance for the reaction is presented. Low molecular weight, volatile, liquid ethers are produced in 6.5% yield; medium molecular weight, nonvolatile, liquid ethers are produced in 4.9% yield; and high molecular weight solids are produced in 56.8% yield of the starting polymer. The major low molecular weight by-products, $CF_4$ and $COF_2$, account for 8.7% and 9.3% of the starting material respectively. The unaccounted for 13.8% of starting material would be comprised of unisolated $CF_4$, as discussed previously, and volatile products produced in the initial stages of the reaction which were not collected. These uncollected products were shown by previous experiments to be mainly small fragment molecules ($CF_4$, $COF_2$, and $C_2F_6$) and a complex mixture of partially fluorinated volatile ethers. Elimination of the partially fluorinated volatile ethers formed in the first part of the reaction from the collected volatile product mixture simplified separation of the desired perfluoroethers by decreasing impurity peaks and peak overlaps in the Glc assay.

EXAMPLE 2

The basic procedure of Example 1 was used employing 40 grams of finely ground (<120 mesh) poly(ethylene oxide)polymer. The initial fluorination conditions were 40 $cm^3min^{-1}$He and 1.0 $cm^3min^{-1}F_2$ at ambient temperature. As the reaction progressed, the temperature remained constant while the gas flow rates were adjusted in a step-wise manner until flow rates of 10 $cm^3min^{-1}$He and 4.0 $cm^3min^{-1}F_2$ were reached. At that point, the gas flow rates were held constant while the temperature was raised from ambient to 110° C. in three 30° C. steps. The volatile products were trapped at −196° C. throughout this reaction, and fractionated on a vacuum line. Pure compounds were isolated by Glc assay of the fractions and were identified by spectroscopic analysis. 9 grams of volatile perfluoroether products were obtained. The composition of the product mixture along with the M.P.'s and B.P.'s of the compounds are shown in the following table together with the $^{19}F$ n.m.r. spectra. Each dimethylether compound exhibited (average values for all the compounds are given here for shifts and coupling constants) a triplet at −16.5 ppm and a quartet at +18.0 ppm with a coupling constant of 9.5 Hz and a singlet at +16.0 ppm relative to 1% aqueous $CF_3CO_2H$ (external). Each methylethylether compound exhibited the same peaks as the dimethylether compounds and an additional singlet at +14.7 ppm. The signal assignments are shown below, and the $^{19}F$ n.m.r. data are given in Table 6.

$CF_3{}^aOCF_2{}^b[CF_2{}^cOCF_2{}^c]_xCF_2{}^bOCF_2{}^a$  (1)

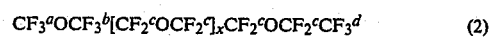
$CF_3{}^aOCF_3{}^b[CF_2{}^cOCF_2{}^c]_xCF_2{}^cOCF_2{}^cCF_3{}^d$  (2)

a; x = 1        d; x = 3
b; x = 1        e; x = 4
c; x = 2

For all compounds the experimental relative intensities of the signals correspond exactly to the calculated relative intensities. No signals were observed for any of the compounds in $^1H$ n.m.r. scans.

TABLE 6

Properties and proportions of compounds (1a–e) and (2a–e) in volatile product mixture. $^{19}F$ n.m.r. shifts in p.p.m. vs. 1% aq. ext. $CF_3CO_2H$, with relative intensities in parentheses for the c resonances.

| Compound | M.p./°C. | B.p./°C. | Mole % in prod. mixt. | $F^a$ (t) ↑ | $F^b$ (q) | $F^c$ (s) | $F^d$ (s) ↑ | $J_{ab}$/Hz |
|---|---|---|---|---|---|---|---|---|
| (1a) | — | — | 14.6 | −16.3 | 18.3 | — | — | 10 |
| (2a) | — | — | 7.6 | −16.3 | 18.2 | 16.2 (4) | 15.0 | 10 |
| (1b) | — | 66–66.5 | 8.7 | −16.4 | 18.2 | 16.1 (2) | — | 9 |
| (2b) | — | 81.5–82 | 4.9 | −16.6 | 18.0 | 16.0 (8) | 14.8 | 9 |
| (1c) | −82 to −80.5 | 104.5–105 | 8.1 | −16.6 | 18.1 | 16.0 (4) | — | 9 |
| (2c) | −80 to −78 | 117.5–118.5 | 5.7 | −16.7 | 18.0 | 15.9 (12) | 14.7 | 9s |
| (1d) | −71 to −69.5 | 138–138.5 | 6.8 | −16.6 | 18.0 | 15.9 (6) | — | 9 |
| (2d) | −60.5 to −60 | 146.5–148 | 5.3 | −16.8 | 17.8 | 15.8 (16) | 14.6 | 10 |
| (1e) | −47 to −46 | 164–164.5 | 5.9 | −16.8 | 17.8 | 15.8 (8) | — | 10 |
| (2e) | −47 to −46 | 173.5–174 | 4.3 | −16.7 | 17.9 | 15.8 (20) | 14.5 | 10 | s — singlet; t — triplet; q — quartet.
↑ Relative intensity 3.    Relative intensity 2.

The gaseous i.r. spectra of all compounds were very similar in showing strong, broad adsorptions between 1125 and 1300 $cm^{-1}$ (C-F stretch and C-O stretch) and several weaker and sharper bands below 1000 $cm^{-1}$.

The mass spectra were recorded with the ion source of the mass spectrometer cooled to room temperature in order to lessen chain fragmentation and rearrangement. For each compound, the highest mass peak observed in the room temperature mass spectrum is the parent minus fluorine peaks, i.e.: for $C_4F_{10}O_2$, 251($C_4F_9O_2+$), for $C_5F_{12}O_2$, 301; for $C_6F_{14}O_3$, 367; for $C_7F_{16}O_3$, 417; for $C_8F_{18}O_4$, 483; for $C_9F_{20}O_4$, 533; for $C_{10}F_{22}O_5$, 599; for $C_{11}F_{24}O_5$, 649; for $C_{12}F_{26}O_6$, 715; and for $C_{13}F_{28}O_6$, 765. By far the most intense peaks of the room temperature spectra were m/e 69($CF_3+$) and 119($C_2F_5+$) with peak intensity decreasing with mass, a characteristic common to many fluorocarbons.

EXAMPLE 3

The procedure of Example 1 were followed except as noted.

Commercially available polypropylene oxide (Polysciences, Inc., MW 4000), which was a viscous oil, was employed. An oil has a low surface area per unit weight, so successful direct fluorination depends upon the ability of fluorine to diffuse into the oil and the ability of HF byproduct to diffuse out. Since the polymer chains of an oil are free to move about, crosslinking would also be a potential complication because of possible chain-radical coupling. Nevertheless, it was decided to fluorinate the polypropylene oxide oil "as is" at ambient temperatures in a room temperature reactor and worry about crosslinking and diffusion problems only if they developed.

Thus, direct fluorination of polypropylene oxide oil was carried out in a room temperature reactor at ambient temperature. This resulted in a more viscous oil with a gel-like surface and only small amounts of volatile products. The "pre-fluorinated" oil was mixed to a uniform consistency and then fluorinated at elevated temperatures to produce significant quantities of volatile products and a very viscous tacky, gel-like, blood-red residue. The reaction conditions for the two-part fluorination process were:

| He (cc/min) | $F_2$ (cc/min) | Temp. (°C.) | Time (days) |
|---|---|---|---|
| 30 | 1.0 | amb. | 4 |
| 20 | 2.0 | amb. | 4 |
| 20 | 2.0 | 70–75 | 2 |
| 20 | 2.0 | 90–95 | 4 |
| 20 | 4.0 | 90–95 | 4. |

The volatile products of the reaction were trapped throughout the reaction at $-196°$ C. in a glass trap and were separated by vacuum line trap-to-trap fractionation into four fractions: $-30°$ (bromobenzene slush), $-78°$ (dry ice), $-131°$ (pentane slush) and $-196°$. For 2.7 g of polypropylene oxide starting material, the described process yielded 2.61 g of solid residue, 0.821 g of volatile compounds in the $-30°$, $-78°$ and $-131°$ fractions and an undetermined amount of small fragment molecules in the $-196°$ fraction.

The blood-red, gel-like, solid residue was analyzed only by infrared spectroscopy. A thin film of the material on a KBr window exhibited a strong absorption in the carbon-hydrogen region ($\sim 3000$ cm$^{-1}$), weak absorptions in the fluorocarbon carbonyl region (1700-1890 cm$^{-1}$) and strong absorptions in the carbon-fluoride/ether carbon-oxygen (1300-1100 cm$^{-1}$) and "fingerprint" (1000-600 cm$^{-1}$) regions. The residue was not analyzed further because volatile perfluoroethers were the desired compounds, and the many residual hydrogens, carbonyl groups, crosslinking (inferred by the gel-like nature of the residue) and polymeric nature of the residue implied an unresolvable, complicated mixture.

The $-196°$ fraction of the volatile product was also analyzed only by infrared spectroscopy. Comparison of the obtained spectra with literature infrared spectra indicated the presence of large amounts of $CF_4$ and $COF_2$ and small amounts of $CO_2$, $C_2F_6$, $C_3F_8$, $SF_6$, $SiF_4$ and possibly $C_4F_{10}$. The estimated quantity of the fraction was several hundred milligrams, and this fraction of trivial, small, fragment molecules was routinely discarded.

The Glc assay of the $-30°$, $-78°$ and $-131°$ fractions resulted in further separation of the more interesting, higher molecular weight volatile products. The Glc separations were characterized by relatively broad peaks, frequently with shoulder peaks or humps, and a significant amount of peak tailing and overlap. These observations implied that the Glc separation was not providing pure compounds but probably mixtures rich in one compound with small amounts of one or more other compounds as impurities. In the attempt to minimize the amount of impurity compounds with the main compound of a Glc "peak", only the centers of the Glc "peaks" were "collected" as each Glc "cut". (The possible reasons for relatively poor separation by Glc are dealt with in the Discussion section.) The Glc "cuts" of the volatile products (vacuum line fraction-retention time) are listed with their produced weights and % yields in Table 7.

TABLE 7

Glc "Cuts" of the $-131°$, $-78°$ and $-30°$
Vacuum Line Fractions of the Polypropylene Oxide
Volatile Products

| Glc "Cut" (Vacuum line fraction–Glc retention time (min)*) | Weight Produced (mg) | Weight % Yield |
|---|---|---|
| 131-3 | 44 | 5.4 |
| 131-7/78-2 | 140 | 17.1 |
| 131-9 | trace+ | — |
| 131-18 | trace+ | — |
| 131-23/78-8 | trace+ | — |
| 78-6 | trace+ | — |
| 78-12 | trace+ | — |
| 78-18 | 48 | 5.8 |
| 78-38 | 93 | 11.3 |
| 30-35 | 51 | 6.2 |
| 30-46 | 35 | 4.3 |
| 30-58 | 27 | 3.3 |
| Unseparated material | 383 | 46.6 |
| Total | 821 mg | 100% |

*Glc Temperature Programs:
$-131°$ Fraction: $-20°$ isothermal
$-78°$ Fraction: 0° for 30 min; 1°/min → 90°
$-30°$ Fraction: 30° for 10 min; 1°/min → 80°
+These "cuts" obtained in larger amounts from preliminary reactions Since only the centers of the Glc peaks were collected, each cut of isolated material was assumed to be a fairly pure compound, and structure determination was attempted, as usual, through infrared, NMR and mass spectral analysis. The infrared spectra of the cuts were all similar in showing no carbon-hydrogen absorptions ($\sim 3000$ cm$^{-1}$), strong and broad absorptions in the carbon-fluorine/ether carbon-oxygen region (1300-1100 cm$^{-1}$) and medium to strong absorptions in the "fingerprint" region (1000-600 cm$^{-1}$). Two of the cuts, 131-3 and 78-12, exhibited strong acyl fluoride infrared bands ($\sim 1880$ cm$^{-1}$), and most of the other cuts also exhibited weak to very weak absorptions in the fluorocarbonyl region (1700-1800 cm$^{-1}$). The weak carbonyl absorptions were interpreted as evidence of fluoroacyl fluorides and fluoroketones being present as the impurities of the Glc cuts. Considering the strong bands of the infrared spectra, the main compound of most Glc cuts was thought to be a perfluoroether, as expected.

NMR analysis was extremely complicated for a couple of reasons. Most important, the $^{19}F$ NMR spectra for fluoroethers with the $CF(CF_3)$—$CF_2$—O repeating unit are second order, ie. the usual multiplet splitting patterns with measurable coupling constants that are so useful for relative position and signal assignments are not observed. The reason for this is the fact that fluorine-fluorine coupling can occur for fluorine nuclei separated by as much as six or seven bonds. The fluorine nuclei in the produced compounds are coupled to many different fluorine nuclei, so broad unresolved NMR signals and second-order spectra resulted. The other complication in NMR interpretation was due to the signals of the impurities. Since all of the compounds produced in the reaction should be of the same general structure, the impurity compounds probably differ in structure from the main compound of the Glc cut only at the end-groups. The impurity compounds would, therefore, exhibit some of the same NMR signals as the main compound and would contribute to the integrated relative intensities of these signals.

The only useful unquestionable information from the $^{19}F$ NMR spectra, therefore, was the chemical shifts of the signals. Intepretation of the spectra was begun by assigning specific structures to the chemical shifts. A review article anionic polymerization of hexafluoropropylene oxide was relied upon for the $^{19}F$ NMR signal assignments for the second-order spectra of the hexamer and heptamer. See Hill, J. T., Macromol, J., Sci.-Chem., A8, 499 (1974).

The applicable assignments were (reference-$CFCl_3$):

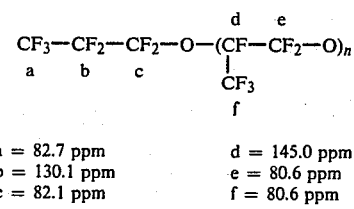

a = 82.7 ppm  d = 145.0 ppm
b = 130.1 ppm e = 80.6 ppm
c = 82.1 ppm  f = 80.6 ppm These reported values are 2-3 ppm lower than the calculated chemical shifts for what is considered to be the same signals of the produced compounds. A 2-3 ppm discrepancy is not large in $^{19}F$ NMR and can often be explained by the way the spectra were recorded and referenced. Our experimental spectra were run with "neat" samples in thinner coaxial tubes inside the NMR tube and referenced by "neat" $CFCl_3$ in a substitute NMR tube. (The thinner tubes "stretched" small samples so $^{19}F$ NMR spectra could be obtained, and the additional glass in the field may alter the overall diamagnetic susceptibility of the sample). With these signal assignments, chemical shift values for the nuclei of the $CF_3$—$CF_2$—O and $CF_3$—O end-groups (from the polyethylene oxide project) and knowledge of approximate chemical shifts of other types of fluorine nuclei, most of the observed signals could be accounted for by fluorine nuclei of perfluoroethers.

The data from the $^{19}F$ NMR spectra of the Glc cuts and the structural assignments for the various chemical shifts is compiled in Table 8.

TABLE 8

$^{19}F$ NMR Data of the Glc "Cuts" of the Polypropylene Oxide Volatile Products Signal Assignment

| Glc "Cut"/$CF_3$O | | $CF_3R_f$ | Internal Pendant $CF_3$ | Internal $CF_2O$/ $CF_3CF_2CF_2O$ | $CF_3CF_2CF_2O$ | $CF_3CF_2O$ | $CF_3CF_2O$ | $R_fCF_2R_f$ | $CF_3CF_2CF_2O$ | Internal —CF—O |
|---|---|---|---|---|---|---|---|---|---|---|
| 131-3 | 59.2 t(11) | | 84.2 (8) | 85.1 t(16) | 86.9, 87.1, 89.6, t(25) d/t pen (45) (8) | 90.7 (6) | 91.8 (6) | 124.9, 125.7 d/quar quar (30) (15) | 133.3 (6) | |
| 131-7/ 78-2 | 59.1 d(2) | 78.0 (4) | | 84.9 (28) | 87.5 (18) | 90.7 (27) | 91.7 (15) | 129.4 (2) | 133.2 (16) | |
| 131-9 | 59.1 t(10) | 76.9 (7) | 84.2 (17) | | 89.4 (6) | 90.5 (6) | 91.6 (6) | 129.3 (5) | | |
| 131-18 | | 76.7 (3) | | 84.8 (12) | 87.1 (4) | 90.5 (5) | 91.6 (3) | 129.2 (4) | 132.9 (5) | |
| 131-23/ 78-8 | 57.2 d/quar (10) | | 83.4 (11) | 86.0 (10) | | 90.6 (10) | 91.7 (7) | | | 149.0 (trace) |
| 78-6 | | | 84.3 (12) | 85.1 (15) | 87.3 pen(4) | 90.7 quar(2) | | | 132.9, 133.2 (3) (4.5) | |
| 78-12 | | 77.3 (5) | | 84.9, 87.6 (15) (8) | | 90.5 (11) | 91.5 (5) | | 132.8 (5) | |
| 78-18 | 59.2 t(2) | | 83.7 (25) | 85.1 (25) | | 90.7 (12) | 91.9 (12) | 126.2, 129.5 (9) (12) | 133.2 (7) | |
| 78-38 | | | 83.4 ⟍ | 84.9 ⟍ (58) | 86.1 ∕ | 90.6 (15) | 91.7 (10) | | 132.8 (10) | 148.0 (4) |
| 30-35 | | | 83.2 ⟍ | 84.9 ⟍ (63) | 86.0 ∕ | 90.5 (11) | 91.4 (7) | | 132.7 (7) | 147.9 (6) |
| 30-46 | | | 83.2 ⟍ | 84.8 ⟍ (65) | 85.8 ∕ | 90.3 ⟍ (12) ∕ | 91.4 | | 132.8 (5) | 147.9 (5) |

TABLE 8-continued

| | | | | 19F NMR Data of the Glc "Cuts" of the Polypropylene Oxide Volatile Products | | | | | |
|---|---|---|---|---|---|---|---|---|---|
| | | | | Signal Assignment | | | | | |
| Glc "Cut"/CF$_3$O | CF$_3$R$_f$ | Internal Pendant CF$_3$ | Internal CF$_2$O/ CF$_3$CF$_2$CF$_2$O | CF$_3$CF$_2$CF$_2$O | CF$_3$CF$_2$O | CF$_3$CF$_2$O | R$_f$CF$_2$R$_f$ | CF$_3$CF$_2$CF$_2$O | Internal —CF—O \| |
| 30–58 | | 83.3 | 85.0 (80) | 86.0 | 90.6 (25) | 91.8 | | 133.0 (3) | 148.1 (3) |

Reference: neat external CFCl$_3$
Data presented as follows: Chemical Shift in ppm
Multiplicity (Integrated Intensity)
All signals are broad unresolved multiplets unless otherwise noted;
d — doublet, t — triplet, quar — quartet, pen — pentet No signals were observed in $^1$H NMR scans for any of the Glc cuts. With the structure assignments of the signals but unreliable integrated intensities, overall molecular weights of the compounds were necessary for structure elucidation. Mass spectrometry was the analytical tool that was useful for molecular weight determination. The mass spectra were characterized by extensive fragmentation and rearrangement, and only when the spectra were run with the ion source of the spectrometer cooled to room temperature were informative high mass peaks. The highest mass peak exhibited by each Glc "cut" was as follows.

| | |
|---|---|
| 131-7/78-2, 285 (C$_5$F$_{11}$O); | 131-23/78-8, 351 (C$_6$F$_{13}$O$_2$); |
| 78-18, 401 (C$_7$F$_{15}$O$_2$); | 78-38, 451 (C$_8$F$_{17}$O$_2$); |
| 30-35, 617 (C$_{11}$F$_{23}$O$_3$); | 30-46, 667 (C$_{12}$F$_{25}$O$_3$); |
| 30-58, 733 (C$_{13}$F$_{27}$O$_4$). | |

(the lowest yield "cuts" 131-9, 131-18, 78-6, 78-12 obtained mainly from preliminary experiments were not analyzed by mass spectrometry). Each highest mass peak is attributed to the parent minus fluorine formula for the major component of the Glc cut. The spectra showed decreasing peak intensity with increasing mass, and the highest intensity peak was always 119(C$_2$F$_5$) or 169(C$_3$F$_7$). The other common low-mass fragment peaks were at m/e 31(CF), 47(COF), 50(CF$_2$), 69(CF$_3$), 81(C$_2$F$_3$), 97(C$_2$F$_3$O), 100(C$_2$F$_4$), 131(C$_3$F$_5$), 135(C$_2$F$_5$O), 147(C$_3$F$_5$O), 150(C$_3$F$_6$), 181(C$_4$F$_7$), 185(C$_3$F$_7$O), 197(C$_4$F$_7$O), 200(C$_4$F$_8$), 213(C$_4$F$_7$O$_2$), 219(C$_4$F$_9$) and 235(C$_4$F$_9$O). The common high-mass fragment peaks were at values corresponding to the empirical formulas: C$_n$F$_{2n-1}$O$_x$ and C$_n$F$_{2n+1}$O$_x$ (x=0–3). High-mass peaks with fewer oxygen atoms than expected for a polypropylene oxide fragment, such as 435(C$_8$F$_{17}$O) and 551(C$_{10}$F$_{21}$O$_2$), was a direct indication of a rearrangement process. The mass spectra were also useful in conclusively establishing the absence of hydrogen in the compounds; none of the peaks always observed for hydrogen-containing fluorocarbons, particularly 51(CF$_2$H), were observed.

In order to test the validity of assigning the highest mass peaks of the mass spectra to parent minus fluorine formulas, several samples were analyzed for molecular weights by the ideal gas method. The experimental results were (Glc cut, gas phase molecular weight, molecular weight implied by mass spectrometry): 131-7/78-2, 307.5, 304; 131-23/78-8, 374, 370; 78-18, 403, 401; 78-38, 466, 470. These confirming values are remarkably accurate considering the Glc cuts were mixtures rich in one compound but with impurities present, and the small analytical samples that were isolated provided only small pressure differences in the standard volume that was used. The three highest molecular weight Glc cuts could not be analyzed for gas phase molecular weights because their vapor pressures at room temperature were too low.

With the mass spectrally-determined molecular weights and the structure assignments for the observed NMR signals, structures could be elucidated for the main compound of several Glc cuts. The compounds were identified by rigorous $^{19}$F NMR analysis, and the structures, parent minus fluorine peaks of the mass spectra and assigned NMR data is listed in Table 9.

TABLE 9

| | | | |
|---|---|---|---|
| | Identified Volatile Compounds from the Fluorination of Polypropylene Oxide with Assigned $^{19}$F NMR Data | | |
| Glc "Cut"/Highest m/e in Mass Spec./ Mol. Wt. of Structure | Identified Compound/ Assigned $^{19}$F NMR Data | Observed Relative Intensity | Theoretical Relative Intensity |
| 131-3 (no Mass Spec.) MW = 166 | CF$_3$—CF$_2$—C(=O)—F  a    b    c a = 87.1 ppm d of t (J = 5.5, 1.5) | 45 | 3 |
| | b = 124.9 ppm d of quart. (J = 9.0, 1.0) | 30 | 2 |
| | c = −19.2 ppm multiplet | 15 | 1 |
| 131-7, 78-2 m/e: 285 (C$_5$F$_{11}$O), P-F MW = 304 (MW$_{gas\ phase}$ = 307.5) | CF$_3$—CF$_2$—CF$_2$—O—CF$_2$—CF$_3$  a    e    b    d    c a = 84.9 ppm | 28 | 3 |
| | b = 87.5 ppm | 18 | 2 |
| | c = 90.7 ppm | 27 | 3 |
| | d = 91.7 ppm | 15 | 2 |
| | e = 133.2 ppm | 16 | 2 |

TABLE 9-continued

Identified Volatile Compounds from the Fluorination of Polypropylene Oxide with Assigned $^{19}$F NMR Data

| Glc "Cut"/Highest m/e in Mass Spec./ Mol. Wt. of Structure | Identified Compound/ Assigned $^{19}$F NMR Data | Observed Relative Intensity | Theoretical Relative Intensity |
|---|---|---|---|
| 131-23, 78-8 m/e: 351 ($C_6F_{13}O_2$), P-F MW = 370 ($MW_{gas\ phase}$ = 374) | $$\begin{array}{c} \quad\quad\quad e\quad\quad\ b \\ CF_3-O-CF-CF_2-O-CF_2-CF_3 \\ f\quad\quad\ \ |\quad\quad\quad\quad d\ \ \ c \\ \quad\quad\quad CF_3 \\ \quad\quad\quad a \end{array}$$ | | |
| | a = 83.4 ppm | 11 | 3 |
| | b = 86.0 ppm | 10 | 2 |
| | c = 90.6 ppm | 10 | 3 |
| | d = 91.7 ppm | 7 | 2 |
| | e = 149.0 ppm | trace | 1 |
| | f = 57.2 ppm d of quart. (J = 15, 4) | 10 | 3 |
| 78-38 m/e: 451 ($C_8F_{17}O$), P-F MW = 470 ($MW_{gas\ phase}$ = 466) | $$\begin{array}{c} \quad\quad\quad\quad\quad\quad\quad h\quad\ b \\ CF_3-CF_2-CF_2-O-CF-CF_2-O-CF_2-CF_3 \\ c\quad\ \ g\quad\ \ d\quad\quad\ |\quad\quad\quad\quad\ f\quad\ \ e \\ \quad\quad\quad\quad\quad\quad\ CF_3 \\ \quad\quad\quad\quad\quad\quad\ a \end{array}$$ | | |
| | a = 83.4 ppm | | |
| | b = 84.4 ppm | | |
| | c = 85.0 ppm  a, b, c, d | 58 | 10 |
| | d = 86.1 ppm | | |
| | e = 90.6 ppm | 15 | 3 |
| | f = 91.7 ppm | 10 | 2 |
| | g = 132.8 ppm | 10 | 2 |
| | h = 148.0 ppm | 4 | 1 |
| 30-35 m/e: 617 ($C_{11}F_{23}O_3$), P-F MW = 636 | $$\begin{array}{c} \quad\quad\quad\quad\quad\quad\quad h\quad\ b \\ CF_3-CF_2-CF_2-O-(CF-CF_2-O)_2-CF_2-CF_3 \\ c\quad\ \ g\quad\ \ d\quad\quad\ |\quad\quad\quad\quad\quad f\quad\ \ e \\ \quad\quad\quad\quad\quad\quad\ CF_3 \\ \quad\quad\quad\quad\quad\quad\ a \end{array}$$ | | |
| | a = 83.2 ppm | | |
| | b = 84.3 ppm | | |
| | c = 84.9 ppm  a, b, c, d | 63 | 15 |
| | d = 86.0 ppm | | |
| | e = 90.5 ppm | 11 | 3 |
| | f = 91.4 ppm | 7 | 2 |
| | g = 132.7 ppm | 7 | 2 |
| | h = 147.9 ppm | 6 | 2 |

In interpreting the NMR spectra, critical evaluation of the experimental integrated intensities of the signals was possible by knowing the molecular weight of the structure. The signals for $CF_3O$ and $CF_3CF_2O$ end-groups, the middle $CF_2$ of perfluoro-n-propyl end-groups and the tertiary CF of the repeating unit usually had accurate experimental integrated intensities. The signals for the other $CF_2$'s and $CF_3$'s of the structure were all close together in the 83–86 ppm region, and the experimental integrated intensities were always higher than expected. The higher values are attributed to signals in the some region from the impurity compounds of the same general structure. Knowing the molecular weight of the structure also assisted in establishing how many signals should be observed, so other weak signals were more easily identified as signals from impurity compounds and excluded from consideration.

The NMR spectra could not be successfully interpreted until some signal assignments by Hill in the low—80 ppm region were changed. Comparing the spectra for our perfluoroethers, particularly $CF_3CF_2CF_2OCF(CF_3)CF_2OCF_2CF_3$ and $CF_3CF_2CF_2O(CF(CF_3)CF_2O)_2CF_2CF_3$, we can see which of the four signals in the region increase in intensity and which remain constant as the number of repeating units increases. The better signal assignments are: $CF_3$ of the repeating unit, ~83.5 ppm; $CF_2$ of the repeating unit, ~84.5 ppm; $CF_3$ of the $CF_3CF_2CF_2O$ end-group, ~85.0 ppm; and $CF_2$ α to the oxygen of the $CF_3CF_2CF_2O$ end-group, ~86.0 ppm. (The assignments for the $CF_3CF_2CF_2O$ end-group were distinguished by integrated intensity.) The questioning of Hill's signal assignments occurred because his published spectra were characterized by wide sweep widths causing sharp signals, so signal assignments for the low—80 ppm region with its numerous overlapping signals would be very difficult. Our spectra were run over narrower sweep widths, so broader signals were obtained. Broadening the low—80 ppm region allowed easier observance of the differences in the region for different compounds and more accurate signal assignments for the region.

Even when the NMR spectra were interpreted with reliable molecular weights, critically evaluated integrated intensities and improved signal assignments in the low—80 ppm region, only four perfluoroether structures could be deduced. The success for those compounds is because their respective Glc cuts probably contained only minor amounts of impurity compounds. The other Glc cuts probably contained larger amounts of impurity compounds with the main compound (or several compounds in equal amounts), so the NMR spectra were too complicated and could not be resolved.

Physical characterization of the four identified perfluoroethers included melting point and boiling point determinations. When the low temperature melting points were measured, it was discovered that the materials solified as glasses instead of crystalline powders when frozen. (This could be due to the presence of impurities or due to the method of quickly freezing the samples by placing them in liquid nitrogen.) The melting points obtained, therefore, were actually glass transition temperatures. Boiling points were determined for the two higher molecular weight perfluoroethers that were identified, but the other two identified perfluoroethers were so volatile that they vaporized from the 4 mm tube of the micro boiling point apparatus before values could be obtained. The observed physical constants were (compound, m.p. (°C.), b.p. (°C.)):

$C_3F_7OC_2F_5$, −122, —; $C_3F_7OCF(CF_3)CF_2OC_2F_5$, −115, 93–94; $CF_3OCF(CF_3)CF_2OC_2F_5$, −120, —; $C_3F_7(OCF(CF_3)CF_2)_2OC_2F_5$, −108, 144–145.

EXAMPLE 4

The procedures of Example 1 were followed except as noted.

Synthesis of Hexafluoroacetone-Ethylene Alternating Copolymer

Equimolar amounts of ethylene and hexafluoroacetone, 0.120 moles of each, were charged into a 30 cc stainless steel autoclave and then irradiated with the 35,000 rads/hr $^{60}Co$ source for three days at −78°. After the reaction, the unreacted monomers were separated and quantitatively analyzed; a 22.4 mole % conversion to polymer was calculated. The white powder copolymer was dissolved in Freon-113 ($CFCl_2CF_2Cl$), filtered and recrystallized by addition of an equal volume of hexane. 4.25 g of fluffy, white, crystalline copolymer was obtained, which is a 18.2% yield. The melting point determined with a Mel-Temp was 99.5°–101° C.; the physical constants determined by Differential Scanning Calorimetry (DSC) were $T_g = -23.4°$ C. ($T_g$ is the glass transition temperature) and $T_{m.p.} = 96.5°$ C. The infrared spectrum of the copolymer (polymer film cast from Freon-113 solution) corresponded exactly to the reported spectrum. Nmr end-group analysis, by the integrated intensities of the internal pendant $CF_3$ at 73.4 ppm and the end-group pendant $CF_3$ at 78.4 ppm, indicated the average degree of polymerization was 360 which corresponds to $MW_{av.} \simeq 70,000$.

Fluorination of Hexafluoracetone-Ethylene Copolymer

The direct fluorination of the copolymer was approached with the same strategy that was successful for the other hydrocarbon polyether polymers, ie. a "pre-fluorination" period that would highly fluorinate the polymer while maintaining its structural integrity, followed by a higher temperature fragmentation period that would produce volatile perfluoroethers.

Since the copolymer was a finely-divided crystalline powder at room temperature, ambient temperatures were expected to be useful for the "perfluorination" period. Such a reaction, however, resulted in conversion of the crystalline polymer to a clear, viscous grease. Infrared analysis of the grease indicated a significant number of residual hydrogens and the presence of acyl fluoride and carboxylic acid end-groups. (Acid end-groups would be due to acyl fluoride hydrolysis by atmospheric moisture while the material was being handled.) Infrared analysis of the volatile products obtained indicated large amounts of $CF_4$ and $COF_2$ and small amounts of partially fluorinated acyl fluorides.

These physical and infrared observations indicated that polymer fragmentation with carbon by carbon end-group degradation was the primary process with only a minor amount of the expected hydrogen-replacing fluorination reaction.

Failure of ambient temperatures for the "pre-fluorination" period led to investigations of sub-ambient temperatures for the "pre-fluorination" conditions. Fluorinations of the copolymer at 0° C. and −25° C. gave similar results to the ambient temperature fluorination. The obtained greases were less dense and viscous, but their infrared spectra again indicated a large amount of functionalization and residual hydrogens. Volatile products were obtained in smaller amounts but were qualitatively similar to those of the ambient temperature reaction. Fluorination of the copolymer at −78° C. had very little effect; the infrared spectrum of the powdery solid product was very similar to that of the starting copolymer, and only traces of the usual volatile products were obtained. Fluorination of the copolymer at −50° C. produced a powdery solid product whose infrared spectrum indicated more reaction than for the −78° C. trial but less functionalization than for the 0° and −25° trials; volatile product formation was also of an intermediate nature. The inescapable conclusion is that the onset of reaction in the direct fluorination of hexafluoroacetone-ethylene copolymer results in chain cleavage at the branched-carbon-oxygen bond and acyl fluoride formation, ie.

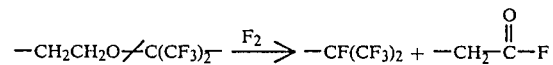

This result was totally unexpected in light of the structural maintenance of the other polyether polymers when subjected to low or ambient temperature direct fluorination.

The most interesting "pre-fluorination" result was obtained when the powdery product of the −50° C. reaction was further fluorinated at −50°, then at stepwise increased temperatures until ambient temperature was reached. The solid product obtained was somewhat sticky but still a powder, and infrared analysis indicated about the same amount of functionalization but a greatly reduced amount of residual hydrogens. A similar experiment with the powdery product of the −78° reaction resulted in a similar powder containing (by IR) few hydrogens and a relatively small amount of functional groups. These reactions also produced larger amounts of the usual volatile products ($CF_4$, $COF_2$ and partially fluorinated acyl fluorides), presumably by a carbon by carbon or segment by segment degradation of the polymer chain ends. These results indicate that careful control of the reaction conditions, temperature and % fluorine in the reactant gas mixture, allows normal fluorination of the hexafluoroacetone-ethylene copolymer after the fluorination has been begun by an unavoidable chain cleavage/acyl fluoride producing process. Operable "pre-fluorination" conditions were determined to be:

| He (cc/min) | $F_2$ (cc/min) | Temp. (°C.) | Time (hours) |
| --- | --- | --- | --- |
| 50 | 1.0 | −50 | 25 |
| 18 | 2.0 | −50 | 8 |
| 8 | 2.0 | −50 | 12 |
| 5 | 4.0 | −50 | 12 |
| 0 | 4.0 | −50 | 18 |

-continued

| He (cc/min) | F$_2$ (cc/min) | Temp. (°C.) | Time (hours) |
|---|---|---|---|
| 0 | 4.0 | −25 | 8 |
| 0 | 4.0 | 0 | 12 |
| 0 | 4.0 | amb. | 12. |

The powdery products with few residual hydrogens were further fluorinated in the attempt to produce the perfluoracyl fluoride-terminated polymers. At ambient temperatures with pure fluorine, longer reaction times were used and high-pressure experiments were tried, but no perfluoro solid products were obtained. All that was obtained was more of the usual volatile products from chain end degradation.

A fragmentation period was then added to the experiment in the attempt to produce volatile perfluoroethers. Fragmentation was promoted, as usual, by the use of elevated temperatures. From the results of the first couple of fragmentation trials, the importance of precise temperature control for fragmentation-fluorination reaction was demonstrated. Fragmentation-fluorination reaction was performed at 75° C. in one reaction and at 65° C., 67° C. then 69° C. in another. The specific reaction conditions were as follows:

| He (cc/min) | F$_2$ (cc/min) | Temp. (°C.) | Time (hours) |
|---|---|---|---|
| Trial # 1 | | | |
| 5 | 4.0 | amb. | 18 |
| 5 | 4.0 | 55 | 24 |
| 5 | 4.0 | 75 | 48 |
| Trial # 2 | | | |
| 5 | 4.0 | amb. | 18 |
| 5 | 4.0 | 65 | 24 |
| 5 | 4.0 | 67 | 24 |
| 5 | 4.0 | 69 | 36. |

The volatile products from the reactions were first separated by vacuum line trap-to-trap fractionation into −196°, −131° and −78° fractions. The −196° fractions from both reactions were very similar and were qualitatively examined only by infrared spectroscopy. Such analysis indicated the fraction contained mostly COF$_2$, and a significant amount of CF$_4$ and small amounts of C$_2$F$_6$, SF$_6$ and SiF$_4$. The fraction was relatively large in quantity, and quantitative analysis (of the −196° fraction of the 65°-67°-69° reaction) by the ideal gas method indicated 6.9 millimoles of compounds. Since the fraction was mostly COF$_2$ and CF$_4$, a reasonable approximation was that the average number of carbon atoms per molecule was one, so 6.9 millimiles of compounds equals 6.9 millimoles of carbon atoms. 0.744 g of starting hexafluoroacetone-ethylene copolymer was used (for the 65°-67°-69° reaction) which corresponds to 3.84 millimoles of repeating units or 19.2 millimoles of carbon atoms. The mole % yield based on carbon of the −196° fraction is, therefore, 35.9%.

The −131° and −78° fractions contained the more interesting, higher molecular weight, perfluoro fragments. Analysis of these fractions obtained from each fragmentation reaction by Glc assay showed that striking differences in the composition of the fractions had resulted. The yields, weight percents and mole percents of the compounds isolated from the −131° and −78° fractions from both reactions are listed in Table 10.

TABLE 10

Yields of Volatile Compounds Produced by Fluorination of Hexafluoroacetone-Ethylene Copolymer

| Compound (Vac. line fraction-Glc retention time) | Yield (mg) Weight % of −131° and −78° Fractions 75° Reaction | Mole % of Starting Polymer+ 65°-67°-69° Reaction |
|---|---|---|
| 131-10* | 258-40.2-16.8 | 201-41.3-17.6 |
| 131-22* | 24-3.7-1.7 | 19-3.9-1.9 |
| 78-30** | 7-1.1-0.5 | 15-3.1-1.4 |
| 78-56** | 191-29.8-13.2 | 123-25.3-11.5 |
| 78-64** | 13-2.0-0.9 | 13-2.6-1.3 |
| 78-92** | trace | 12-2.4-1.2 |
| 78-104** | trace | 47-9.7-4.5 |
| Unseparated Material | 148-23.1 | 57-11.7 |
| Total | 641  100% | 487  100% |

*Glc Temperature Program: −50° for 12 min; 10°/min → 100°
**Glc Temperature Program: 0° for 10 min; 1°/min → 100°
+Calculation: (g compound) ÷ (MW compound) × (# carbon atoms in compound) = Moles of carbon atoms in compound
(Moles of carbon atoms in compound) ÷ (Moles of carbon atoms in starting polymer) = Mole % Yield
For 75° reaction - 1.003 g starting polymer = 25.85 millimoles carbon
For 69° reaction - 0.744 g starting polymer = 19.2 millimoles carbon The data indicate that the reaction at 75° produced primarily two volatile perfluoro species with only traces of other products, while the 65°-67°-69° reaction produce larger, isolatable quantities of other interesting volatile species along with the two high-yield products. An important observation for the 65°-67°-69° reaction was that very small quantities of volatile products were produced at the 65° and 67° temperatures; only when 69° was reached did significant fragmentation and volatile product formation occur. Also noted was the fact that the 75° reaction caused complete fragmentation of the substrate to volatile products and left essentially no solid residue, while from the 65°-67°-69° reaction, 196 mg of solid product was obtained (which is described later). All of these observations indicate that a fragmentation threshhold temperature exists between 65° C. and 75° C., and careful control of the fragmentation temperature allows control over the types and amounts of volatile products that are produced.

The structures of the two compounds isolated from the −131° fraction were readily determined by spectral analysis. The reactions' highest-yield compound, 131-10, was identified as perfluoroisobutane, (CF$_3$)$_3$CF, by a peak to peak match of the experimental infrared spectrum with a literature infrared spectrum. The identifying infrared absorption bands were (cm$^{-1}$): 1330-1260 (broad, strong, 3-peak pattern), 1200 (w), 1170 (m), 995 (s) and 730 (m). The $^{19}$F NMR spectrum of the compound confirmed the structure: CF$_3$ region—76.3 ppm, doublet (J=6 Hz); CF region—190.1 ppm, dectet expected but only eight peaks clearly evident (J=6 Hz); relative integrated intensities—9 to 1.

The compound 131-22 was identified as (CF$_3$)$_2$CFCF$_2$C(O)F, perfluoroisovaleryl fluoride. Its infrared spectrum exhibited strong acyl fluoride (1890 cm$^{-1}$) and carbon-fluorine (1240-1330 cm$^{-1}$) stretches. The mass spectrum showed a parent minus fluorine peak at m/e 247(C$_5$F$_9$O). The $^{19}$F NMR data was the most useful information for structure determination; the observed signals and their assignments were:

|  | Shift, (ppm) | Splitting, | Coupling, (Hz) | Rel. Int. |
|---|---|---|---|---|
| (CF$_3$)$_2$—CF—CF$_2$—C—F<br>  a    b    c    d<br>                       ‖<br>                       O | a - 74.9,<br>b - 188.2,<br>c - 115.8,<br>d - not observed | t of d,<br>septet,<br>septet<br>of d, | 10.5/6,<br>~6,<br>10.5/5, | 6<br>1<br>2 |

The acyl fluoride fluorine nucleus was not observed in the $^{19}$F NMR spectrum, so the infrared spectrum was rerun for reaffirmation of the acyl fluoride group. No acyl fluoride absorption was observed, but an OH stretch (3580 cm$^{-1}$), two carbonyl stretches (1820 and 1780 cm$^{-1}$, assigned to the monomeric and associated forms of a carboxylic acid, respectively) and the same carbon-fluorine and "fingerprint" absorptions were observed. The rationalization is that poor vacuum line technique was used allowing water to be condensed with the sample which caused hydrolysis to (CF$_3$)$_2$CFCF$_2$COOH. The doublet splitting (J=5 Hz) of the CF$_2$ is thought due to coupling with the CF. The CF was, therefore, coupled almost equally to the CF$_3$ groups (J=6 Hz) and CF$_2$ group (J=5 Hz), so a nonet with broad peaks would be expected; the peaks of the CF envelope were indeed broad but only the middle seven of the expected nine were clearly evident.

The five compounds isolated from the −78° fraction were spectrally identified as the structurally-novel, branched perfluoroethers expected from the reaction. Their infrared spectra were all similar in showing a strong, broad absorption in the carbon-fluorine and ether carbon-oxygen region (1350–1100 cm$^{-1}$) and the same strong, sharp absorptions in the "fingerprint" region at 1000–990 cm$^{-1}$, 900–890 cm$^{-1}$, 760 cm$^{-1}$ and 735 cm$^{-1}$. Each spectrum also exhibited other, weaker, non-general signals on the fingerprint region. The infrared spectra were very similar to those obtained for the perfluoroethers produced from polyethylene oxide and polypropylene oxide polymers.

Mass spectrometry, as for the other perfluoroether projects, was useful for determining the molecular weights of the isolated compounds. The spectra were characterized, as usual, by extensive fragmentation, rearrangement and decreasing peak intensity with increasing mass. Only when the spectra were run with the ion source of the mass spectrometer cooled to room temperature were the informative high mass peaks up to and including the parent minus fluorine peak observed; the parent minus fluorine peaks for the five perfluoroethers are listed in Table 11.

TABLE 11

$^{19}$F NMR Data and Structures of Perflouroethers from the Fluorination of Hexafluoroacetone-Ethylene Copolymer

| Compound/Glc Retention Time/<br>Highest m/e in Mass Spec. | Assigned $^{19}$F NMR Data | Relative Intensities Obs. | Theor. |
|---|---|---|---|
| (CF$_3$)$_2$CFOCF$_2$CF$_2$CF(CF$_3$)$_2$<br>  b    e    c    d    f    a<br>Glc r. t.: 30<br>m/e: 435 (C$_8$F$_{17}$O), P-f | a: 75.2 ppm octet (J = 8.5)<br>b: 83.4 ppm t (J = 5)<br>c: 82.5 ppm m<br>d: 120.1 ppm septet (J = 11.5)<br>e: 147.0 ppm t (J = 22)<br>f: 187.9 ppm m | 16<br>16<br>6<br>5<br>3<br>2.5 | 6<br>6<br>2<br>2<br>1<br>1 |
| (CF$_3$)$_3$COCF$_2$CF$_2$CF(CF$_3$)$_2$<br>  a         c   d    e   b<br>Glc r. t.: 56<br>m/e: 485 (C$_9$F$_{19}$O), P-F | a: 72.9 ppm t (J = 9.5)<br>b: 75.2 ppm octet (J = 5.8)<br>c: 81.8 ppm m<br>d: 119.7 ppm septet (J = 11.5)<br>e: 188.0 ppm m | 165<br>106<br>34<br>34<br>17 | 9<br>6<br>2<br>2<br>1 |
| (CF$_3$)$_2$CFOCF$_2$CF$_2$C(CF$_3$)$_2$OCF$_2$CF$_3$<br>  b    g    d    f    a          e    c<br>Glc r. t.: 64<br>m/e 551 (C$_{10}$F$_{21}$O$_2$), P-F | a: 72.3 ppm m<br>b: 84.0 ppm t (J = 5)<br>c: 88.1 ppm m<br>d: 73.6 ppm m<br>e: 89.0 ppm m<br>f: 118.9 ppm m<br>g: 146.5 ppm t (J = 20) | 10<br>9<br>4<br>3<br>2.5<br>3<br>1.5 | 6<br>6<br>3<br>2<br>2<br>2<br>1 |
| (CF$_3$)$_2$CFOCF$_2$CF$_2$C(CF$_3$)$_2$OCF$_2$CF$_2$CF(CF$_3$)$_2$<br>  c    h    d    f    a          e    g    i    b<br>Glc r. t.: 92<br>m/e: 701 (C$_{13}$F$_{27}$O$_2$), P-f | a: 69.7 ppm m<br>b: 74.8 ppm octet (J = 5.8)<br>c: 82.9 ppm t (J = 5)<br>d: 71.9 ppm m<br>e: 80.3 ppm m<br>f: 116.3 ppm m<br>g: 118.7 ppm septet (J = 11.5)<br>h: 147.0 ppm t (J = 20)<br>i: 187.7 ppm m | 7.5<br>8<br>7<br>3<br>3<br>3<br>2.5<br>1<br>1.5 | 6<br>6<br>6<br>2<br>2<br>2<br>2<br>1<br>1 |
| (CF$_3$)$_3$COCF$_2$CF$_2$C(CF$_3$)$_2$OCF$_2$CF$_2$CF(CF$_3$)$_2$<br>  b       d    f    a          e    g    h    c<br>Glc r. t.: 104<br>m/e: 751 (C$_{14}$F$_{29}$O$_2$), P-F | a: 69.8 ppm m<br>b: 72.3 ppm t (J = 9.5)<br>c: 74.8 ppm octet (J = 5.8)<br>d: 79.3 ppm m<br>e: 80.8 ppm m<br>f: 115.7 ppm m<br>g: 118.8 ppm septet (J = 11.5)<br>h: 187.8 ppm m | 24<br>35<br>25<br>7<br>7.5<br>7.5<br>8<br>4 | 6<br>9<br>6<br>2<br>2<br>2<br>2<br>1 |

The common low-mass peaks were at m/e 31(CF), 44(CO$_2$), 47(COF), 50(CF$_2$), 69(CF$_3$), 81(C$_2$F$_3$), 93(C$_3$F$_3$), 97(C$_2$F$_3$O), 100(C$_2$F$_4$), 119(C$_2$F$_5$), 131(C$_3$F$_5$), 150(C$_3$F$_6$), 169(C$_3$F$_7$), 181(C$_4$F$_7$), 197(C$_4$F$_7$O), 200(C$_4$F$_8$), 219(C$_4$F$_9$), 231(C$_5$F$_9$), 235(C$_4$F$_9$O), 247(C$_5$F$_9$O), 269(C$_5$F$_{11}$) and—285(C$_5$F$_{11}$O). The common high-mass peaks from the higher molecular weight compounds were at m/e values corresponding to the empirical formulas C$_n$F$_{2n-1}$O$_x$, C$_n$F$_{2n}$O$_x$ and C$_n$F$_{2n+1}$O$_x$ (x=1–3). The presence of low intensity "two oxygen peaks" in the spectra of the monoethers and "three oxygen peaks" in the spectra of the diethers is evidence of a complicated rearrangement process. Again, the lack of peaks at m/e 51 ($CF_2H$) and 101 ($C_2F_4H$), the peaks always observed for highly fluorinated, hydrogen-containing compounds, proved the compounds were perfluoro.

$^{19}F$ NMR analysis was, again, the most useful spectral method for structure determination. The perfluoroethers' $^{19}F$ NMR signals, their assignments, observed relative intensities and theoretical relative intensities are listed in Table 12. The average chemical shifts of the various fluorine nuclei were as follows (in ppm from neat external $CFCl_3$):

$CF_3$ of isopropyl end-groups 83.4; $CF_3$ of t-butyl end-groups 72.6;
$CF_3$ of isoamyl end-groups 75.0; Internal pendant $CF_3$ 70.6;
All $CF_2$—O 79.9; All internal $CF_2$ 118.3;
CF of isopropyl end-groups 146.8; CF of isoamyl end-groups 187.8. The fluorine-fluorine coupling patterns observed are good examples of the unpredictable and unusual coupling characteristics in $^{19}F$ NMR spectroscopy. The $CF_3$ groups and CF of isopropyl end-groups do not couple to one another, but each couples to the nearest $CF_2$ "across" the oxygen with average coupling constants of 21 Hz and 5 Hz, respectively. The $CF_3$ groups of the tertiary-butyl groups also couple "across" the oxygen to the nearest $CF_2$ with a coupling constant of 9.5 Hz. The coupling observed for the signals of the isoamyl end-group was the most interesting; the internal $CF_2$ is always a septet with $J\simeq11.5$ Hz, and the $CF_3$ groups always appear as octets with $J\simeq5.8$ Hz. The explanation is that the six fluorines of the two $CF_3$ units couple to the internal $CF_2$ with $J\simeq11.5$ Hz (the internal $CF_2$ is coupled to no other nuclei, so it is a septet), and they also couple to the other three fluorines of the end-group equally and with exactly half the coupling constant of the internal $CF_2$ coupling, ie. $\sim 5.8$ Hz. The result for the $CF_3$ groups is a triplet ($J\simeq11.5$ Hz) of quartets ($J\simeq5.8$ Hz) which is indistinguishable from a 5.8 Hz octet. The signals for the other three fluorines of the isoamyl end-group and for all the fluorines of the internal —$CF_2CF_2C(CF_3)_2O$— groups appeared as broad unresolved multiplets, so no additional conclusions as to coupling trends can be made.

Physical characterization of the isolated perfluoroethers involved melting point and boiling point determinations. In attempts to measure melting points, the problem of freezing to glasses instead of crystalline powders occurred again for several of the samples. Therefore, the solid to liquid phase change temperatures for those samples are actually glass transition temperatures ($T_g$) instead of crystalline melting points. Boiling points could only be measured for two of the perfluoroethers because the others were not obtained in sufficient yields. The measured physical constants were:

As stated previously, the fragmentation period of the 65°-67°-69° reaction did not convert all of the polymeric substrate to volatile products. A small amount (196 mg) of sticky, white powder remained in the reaction boat. Infrared analysis (KBr pellet) of the solid showed the usual strong broad carbon-fluorine and ether carbon-oxygen stretches at 1350-1100 cm$^{-1}$ with only very weak absorptions in the carbon-hydrogen (3000 cm$^{-1}$) and fluorocarbon acid (1800 cm$^{-1}$) regions. This suggests that the residue is more highly fluorinated than the product of the "pre-fluorination" phase of the reaction, but the perfluoro polymer still has not been obtained. $^{19}F$ NMR end-group analysis was attempted in order to determine an average molecular weight for the material, but the solid was only very slightly soluble in the best solvent ($CFCl_2CF_2Cl$), and only very weak signals attributable to the fluorines of the —$CF_2CF_2C(CF_3)_2O$— repeating unit were observed.

Those skilled in the art will recognize, or be able to ascertain using no more than routine experimentation, many equivalents to the specific reactants, reaction conditions, steps, apparatus, etc., described herein as preferred embodiments. Such equivalents are intended to be encompassed within the scope of the following claims.

What is claimed is:

1. A method for forming fluorocarbon ethers having perfluoralkyl groups, comprising:
   a. fluorinating a high molecular weight polyether under conditions which produce a fluorinated polyether;
   b. subjecting said fluorinated polyether to a temperature which is higher than the temperature used in the conditions in step a, and between approximately 55° C. and 210° C. to cause a controlled fragmentation of said polyether into lower molecular weight fluorocarbon ether compounds; and
   c. separating said fluorocarbon ether compounds from the reaction mixture.

2. A method of claim 1, where said fluorination is carried out with elemental fluorine gas.

3. A method of claim 1, where said high molecular weight polyether is perfluorinated to a perfluoropolyether.

4. A method of claim 1, where said high molecular weight polyether compound comprises a polyalkylene oxide ether wherein said alkylene group contains at least two carbon atoms.

5. A method of claim 4 wherein said poly(alkylene oxide)ether comprises polypropylene oxide.

6. A method of claim 1, where the high molecular weight polyether is polyethylene oxide and the lower molecular weight fluorocarbon ether compounds have the formula $R_f$—O—($CF_2$—$CF_2$—O)$_n$—$R_f$, where n is 1-6 and $R_f$ is $CF_3$ or $C_2F_5$.

* * * * *

|  | M.P. | B.P. |
|---|---|---|
| $(CF_3)_2CFOCF_2CF_2CF(CF_3)_2$ | −120 ($T_g$) | — |
| $(CF_3)_3COCF_2CF_2CF(CF_3)_2$ | −56 to −57.5 | 118.5-119.5 |
| $(CF_3)_2CFOCF_2CF_2C(CF_3)_2OCF_2CF_3$ | −110 ($T_g$) | — |
| $(CF_3)_2CFOCF_2CF_2C(CF_3)_2OCF_2CF_2CF(CF_3)_2$ | −95 ($T_g$) | — |
| $(CF_3)_3COCF_2CF_2C(CF_3)_2OCF_2CF_2CF(CF_3)_2$ | −61 to −63 | 190.5-191.5 |

UNITED STATES PATENT AND TRADEMARK OFFICE
CERTIFICATE OF CORRECTION

PATENT NO. : 4,523,039

DATED : June 11, 1985

INVENTOR(S) : Lagow et al.

It is certified that error appears in the above-identified patent and that said Letters Patent is hereby corrected as shown below:

Column 1, line 28 delete "M. S.," and insert --M. A.,--
Column 6, line 32 delete "wit" and insert --with--
Column 7, line 3 delete "OF-1-0065" and insert --QF-1-0065--
Column 8, line 15 delete the paragraph indentation
Column 8, line 39 delete "b - 3" and insert --b = 3--
Column 8, line 43 delete "a - 5" and insert --a = 5--
Column 9, line 7 delete "740(w)," and insert --740(m),--
Column 10, line 9 delete "b - 4," and insert --b = 4,--
Column 10, line 10 delete "b - 5," and insert --b = 5,--
Column 10, line 11 delete "b - 6," and insert --b = 6,--
Column 10, line 21 delete "descending" and insert --decreasing--
Column 10, line 23 underline Adv. Fluorine Chem.
Column 11, line 38 after 11.98 insert --%--
Column 12, line 10 after volatility delete ":" and insert --;--
Column 12, line 37 delete "amoung" and insert --amount--

Column 14, line 32 delete "$CF_3{}^a OCF_2{}^b [CF_2{}^c OCF_2{}^c]_x CF_2{}^b OCF_2{}^a$" and insert --$CF^a{}_3 OCF^b{}_2 [CF^c{}_2 OCF^c{}_2]_x CF^b{}_2 OCF^a{}_2$--

Column 14, line 34 delete "$CF_3{}^a OCF_3{}^b [CF_2{}^c OCF_2{}^c]_x CF_2{}^c OCF_2{}^c CF_3{}^d$" and insert --$CF^a{}_3 OCF^b{}_3 [CF^c{}_2 OCF^c{}_2]_x CF^c{}_2 OCF^c{}_2 CF^d{}_3$--

Column 14, line 36 delete "a; x = 1" and insert --a; x = 0--
Column 14, line 39 after compounds insert --,--

Column 14, line 48 after $F^b(q)$ insert --‡--
Column 14, line 58 delete "14.5" and insert --14.6--
Column 14, line 60 before Relative intensity 2. insert --‡--

UNITED STATES PATENT AND TRADEMARK OFFICE
CERTIFICATE OF CORRECTION

PATENT NO. : 4,523,039

DATED : June 11, 1985

INVENTOR(S) : Lagow et al.

It is certified that error appears in the above-identified patent and that said Letters Patent is hereby corrected as shown below:

Column 14, line 62 delete "adsorptions" and insert
  --absorptions--
Column 15, line 2 after ($C_4F_9O_2+$) delete "," and insert --;--

Column 15, line 12 delete "procedure" and insert --procedures--
Column 15, line 52 delete "2.7 g" and insert --2.76 g--
Column 16, line 3 delete "product" and insert "products"
Column 18, line 1-2 underline Macromol, J., Sci. Chem.
Column 18, line 25 delete ")." and insert --.)--
Column 18, line 58 delete "84.9, 87.6" and insert --84.9, 85.6--
Column 19, line 25 delete "peaks." and insert
  --peaks observed.--
Column 19, line 29 delete "($C_5H_{11}O$);" and insert --($C_5F_{11}O$);--

Column 19, line 29 delete "($C_6H_{13}O_2$);" and insert --($C_6F_{13}O_2$);--

Column 20, line 15 after formulas delete ":"
Column 21, line 58-59 do not hyphenate low
Column 28, line 38 after m/e insert --:--

Signed and Sealed this

Sixth Day of May 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,523,039

DATED : June 11, 1985

INVENTOR(S) : Richard J. Lagow

It is certified that error appears in the above-identified patent and that said Letters Patent is hereby corrected as shown below:

Column 30, line 29, "groups" should read -- end groups --.

Signed and Sealed this

Twelfth Day of August 1986

[SEAL]

Attest:

DONALD J. QUIGG

Attesting Officer

Commissioner of Patents and Trademarks